United States Patent [19]
Zavilla et al.

[11] Patent Number: 5,780,682
[45] Date of Patent: Jul. 14, 1998

[54] PROCESS FOR THE SYNTHESIS OF FLUORINATED ALKYL SULPHONYL HALIDES

[75] Inventors: John Zavilla, Vedæk; Sven Ivar Hommeltoft, Hillerød, both of Denmark

[73] Assignee: Haldor Topsoe A/S, Lyngny, Denmark

[21] Appl. No.: 934,204

[22] Filed: Sep. 19, 1997

Related U.S. Application Data

[63] Continuation-in-part of Ser. No. 626,324, Apr. 2, 1996, abandoned.

[30] Foreign Application Priority Data

Apr. 4, 1995 [DK] Denmark ................. 0383/95

[51] Int. Cl.$^6$ ................. C07C 315/04
[52] U.S. Cl. ................. 568/35; 568/28
[58] Field of Search ................. 560/28; 568/35

[56] References Cited

U.S. PATENT DOCUMENTS

| | | | |
|---|---|---|---|
| 2,732,398 | 1/1956 | Brice et al. | 260/503 |
| 2,877,267 | 3/1959 | Tiers et al. | 260/543 |
| 3,542,864 | 11/1970 | Koshar | 260/543 |

FOREIGN PATENT DOCUMENTS

| | | |
|---|---|---|
| 1573537 | 7/1968 | France. |
| 1668584 | 2/1968 | Germany. |
| 1912738 | 3/1969 | Germany. |
| 2725211 | 6/1977 | Germany. |
| 4208364 | 3/1992 | Germany. |
| 4218562 | 6/1992 | Germany. |
| 4226758 | 8/1992 | Germany. |

OTHER PUBLICATIONS

Hawley's Condensed Chemical Dictionary, R Lewis ed., 1993 pp. 9 and 416, 1993.
General College Chemistry by Keenan and Wood, 4th ed., pp. 194 and 195, 1981.

Mechanism and Theory in Organic Chemistry, 2nd ed. p. 164, 1971.

Q.A. Radchenko, et al., "Perfluoroisoalkanesulfinic And Perfluoroisoalkanesulfonic Acids", *Institute of Organic Chemistry, Academy of Sciences of the Ukrainilan SSR*, vol. 14, No. 2, pp. 251–254.

Hsu-Nan Huang, et al., "Novel Synthesis of Unusual Classes of Fluorocarbon Organosulfur Compounds Using Elemental Fluorine as a Reagent", *Inorg. Chem.* 1991, vol. 30, No. 4, pp. 789–794.

Stanley Temple, "The Reaction of Sullfuryl Fluoride and Sulfonyl Fluorides with Fluoro Olefins", The Journal of Organic Chemistry, vol. 33, No. 1 Jan. 1968.

*Primary Examiner*—Gary Geist
*Assistant Examiner*—Jean F. Vollano
*Attorney, Agent, or Firm*—Ostrolenk, Faber, Gerb & Soffen, LLP

[57] ABSTRACT

Preparation of fluorinated alkyl sulphonyl halides having the general formula:

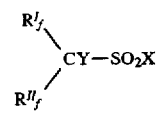

where $R'_f$ is fluorinated alkyl group and $R''_f$ is a fluorinated alkyl group or fluorine, X is a halogen atom, and Y is a proton, a halogen atom, or a fluorinated alkyl groups, by reaction of a corresponding fluorinated unsaturated hydrocarbon with sulphuryl halide, wherein the reaction is carried out in the presence of at least catalytic amounts of a fluoride in a solvent comprising compounds having one or more SO and/or $SO_2$ groups incorporated in the compound structure.

13 Claims, No Drawings

PROCESS FOR THE SYNTHESIS OF FLUORINATED ALKYL SULPHONYL HALIDES

This is a continuation-in-part of application Ser. No. 08/626,324 filed on Apr. 2, 1996; now abandoned.

The present invention is directed to the preparation of fluorinated alkyl sulphonyl halides. In particular, the invention provides a process for the preparation of those compounds by employing a specific solvent to obtain high yield in the synthesis of fluorinated alkyl sulphonyl halides.

Polyfluoro and perfluoro alkyl sulphonyl fluorides are presently prepared by a number of methods, including electrochemical fluorination of the corresponding alkyl sulphonyl halides or cyclic sulphones, using anhydrous HF (U.S. Pat. No. 2,732,398, DE Offenlegungsschrift No. 1,912,738, DE Offenlegungsschrift No. 2,725,211, DE Offenlegungsschrift No. 4,208,364, DE Offenlegungsschrift No. 4,218,562, DE Offenlegungsschrift No. 4,226,758) or elemental fluorine (Inorg. Chem. 30 (1991) 789–794).

It is further known to use a multistep synthesis, where the final step is the reaction of the corresponding perfluoro alkyl sulphonyl chloride with cesium fluoride, giving the acid fluoride (Zh. Org. Khim. 14 (1978) 275–278). Preparation of polyfluorinated alkyl sulphonyl fluorides by addition of sulphuryl chloride fluoride to a perfluoro-olefin is disclosed in U.S. Pat. No. 2,877,267 and perfluorinated alkyl sulphonyl fluorides by addition of sulphuryl fluoride to a perfluoro-olefin is disclosed in FR Patent No. 1,573,537, U.S. Pat. No. 3,542,864, DE Auslegeschrift No. 1,668,584 and J. Org. Chem. 33 (1968) 344–346.

By electrochemical fluorination, it is possible to synthesize linear perfluoro-alkyl sulphonyl fluorides of variable chain length, whereas acid fluorides having a branched perfluoroalkyl chain only are obtainable in poor yields. Thus, it is reported that perfluoro-i-propyl sulphonyl fluoride has been prepared by the direct fluorination of i-propyl sulphonyl fluoride using elemental fluorine (Inorg. Chem. 30 (1991) 789–794).

The reaction is carried out in a four-zone cryogenic reactor with a reaction time of 9 days, at temperatures between +100° C. and ambient, yielding 0.96 g (29%) of perfluoro-i-propyl sulphonyl fluoride.

A further synthesis route for the preparation of branched perfluoro alkyl sulphonyl fluorides comprises addition of sulphuryl fluoride to perfluoro-olefins in a suitable solvent in the presence of catalytic amounts of fluoride ions, e.g. synthesis of perfluoro-i-propyl sulphonyl fluoride by the addition of sulphuryl fluoride to perfluoro-propen using different combinations of solvent and fluoride donors.

We have now found that fluorinated alkyl sulphonyl halides are prepared with a considerably higher yield than by the known processes, when carrying out the reaction of sulphuryl halide with fluorinated unsaturated hydrocarbons in the presence of catalytic amounts of fluoride salts and in a solvent comprising compounds having incorporated —$SO_2$— or —SO— groups in their structure.

Pursuant to this finding, the invention provides an improved process for the preparation of fluorinated alkane sulphonyl halides having the general formula:

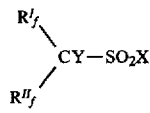

where $R'_f$ is a fluorinated alkyl group, $R''_f$ is a fluorinated alkyl group or fluorine, X is a halogen atom, and Y is a proton, a halogen atom, or a fluorinated alkyl group, by reacting a corresponding fluorinated unsaturated hydrocarbon with a sulphuryl halide, wherein the reaction is carried out in the presence of at least catalytic amounts of fluoride in a solvent comprising compounds having one or more SO and/or $SO_2$ groups incorporated in the compound structure.

Solvents used in the known synthesis processes are diethyleneglycol dimethylether, acetonitrile and N,N-dimethyl formamide, which belong to the category of aprotic polar solvents. Those solvents have a moderately high dielectric constant and the ability to dissolve at least catalytic amounts of inorganic salts.

The —SO— or —$SO_2$— group containing compounds, used in the invention, have a similar dielectric constant to that of the solvents used in the known processes.

As a theoretical explanation, the higher product yield obtained by use of —SO— or —$SO_2$— group containing compounds as solvent in the synthesis of fluorinated alkane sulphonyl halides may be provided through the presence of —SO— or —$SO_2$— groups or more specific through the structure S=O, which by its configuration is similar to the structure of the sulphuryl halide reagent and the fluorinated alkyl sulphonyl halide product.

Typical —SO— and —$SO_2$— group containing compounds for use as solvent in the invention are alkyl sulphonyl and alkyl sulphoxide compounds.

Presently, the most preferred compound is tetramethylene sulphone as solvent for use in the above process alkyl sulphoxide compounds wherein the total number of carbon atoms is at least three are especially contemplated.

EXAMPLE 1

Preparation of perfluoro-i-propyl sulphonyl fluoride

Chemicals

Perfluoro-propene (−29° C.), Heraeus. Sulphuryl fluoride (bp: −53° C.), synthesized in the lab. Tetramethylene sulphone (99%, mp: 28° C., bp: 285° C.), Heraeus. Dried with molecular sieves (3 Å). Potassium fluoride, Riedel-de Haën Dried at 200° C. (48 hr).

Into a clean dry Parr-reactor (stainless steel, vol: 2 liter) 400 ml of tetramethylene sulphone were loaded together with 46 g of potassium fluoride. The reactor was sealed, flushed with dry nitrogen, evacuated, cooled in a dry ice/acetone mixture and loaded with 565 g of sulphuryl fluoride. The reactor was heated to 30° C., placed in an oven and heated to 140° C. under vigorous stirring. 635 g of perfluoro propene were then introduced into the reactor over a period of 6 hr, resulting in a pressure drop from 995 psi to 508 psi. Subsequently, the reaction mixture was cooled and distilled at atmospheric pressure. A product fraction was recovered within the boiling range of 0°–39° C. as 1032.2 g colourless liquid consisting of $(CF_3)_2CFSO_2F$ including small amounts of $(CF_3)_2CFH$. Product yield: 72%.

What is claimed is:

1. A method for the preparation of fluorinated alkyl sulphonyl haides having the generic formula:

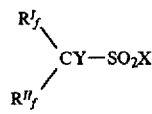

where $R'f$ is a fluorinated alkyl group and $R''f$ is a fluorinated alkyl group or fluorine, X is a halogen atom, and Y is a proton, a halogen atom, or a fluorinated alkyl group, comprising reacting a corresponding fluorinated unsaturated hydrocarbon with sulphuryl halide, wherein the reaction is carried out in the presence of at least catalytic amounts of a fluoride in a solvent comprising an alkyl sulphonyl or alkyl sulphoxide compound wherein the total number of carbon atoms in the alkyl sulphoxide compound is at least 3.

2. Process according to claim 1, wherein the solvent comprises tetramethylene sulphone.

3. Process according to claim 1, wherein the sulphuryl halide is a sulphuryl fluoride halide.

4. Process according to claim 1, wherein the sulphuryl halide is sulphuryl fluoride.

5. Process according to claim 1, wherein the fluoride is an alkali metal fluoride.

6. Process according to claim 1, wherein the fluoride is potassium fluoride.

7. Process according to claim 2, wherein the fluoride is an alkali metal fluoride.

8. Process according to claim 7, wherein the fluoride is potassium fluoride.

9. Process according to claim 8, wherein the sulphuryl halide is sulphuryl fluoride.

10. Process according to claim 3, wherein the fluoride is an alkali metal fluoride.

11. Process according to claim 10, wherein the fluoride is potassium fluoride.

12. A method for the preparation of fluorinated alkyl sulphonyl halides having the generic formula:

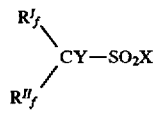

where $R'_f$ is a fluorinated alkyl group and $R''_f$ is a fluorinated alkyl group or fluorine, X is a halogen atom and Y is a proton, a halogen atom or a fluorinated alkyl group, comprising reacting a corresponding fluorinated unsaturated hydrocarbon with sulphuryl halide in the presence of at least catalytic amounts of a fluoride in a solvent comprising an alkyl sulphonyl or alkyl sulphoxide compound excluding sulphuryl and thionyl halides and dimethyl sulfoxide.

13. Process according to claim 12, wherein the solvent comprises tetramethylene sulphone.

* * * * *